US009816985B2

(12) United States Patent
Murphy et al.

(10) Patent No.: US 9,816,985 B2
(45) Date of Patent: Nov. 14, 2017

(54) METHOD FOR PREDICTING RISK OF EXPOSURE TO INTERSTITIAL FIBROSIS AND TUBULAR ATROPHY WITH CLUSTERIN

(71) Applicants: Icahn School of Medicine at Mount Sinai, New York, NY (US); Westmead Institute For Medical Research, Westmead (AU); Western Sydney Local Health District, Westmead (AU)

(72) Inventors: Barbara Murphy, Pelham Manor, NY (US); Philip J. O'Connell, Sydney (AU)

(73) Assignees: Icahn School of Medicine at Mount Sinai, New York, NY (US); Westmead Institure For Medical Research, Westmead (AU); Western Sydney Local Health District, Westmead (AU)

( * ) Notice: Subject to any disclaimer, the term of this patent is extended or adjusted under 35 U.S.C. 154(b) by 0 days.

(21) Appl. No.: 14/394,965

(22) PCT Filed: Apr. 17, 2013

(86) PCT No.: PCT/US2013/037002
§ 371 (c)(1),
(2) Date: Oct. 16, 2014

(87) PCT Pub. No.: WO2013/158777
PCT Pub. Date: Oct. 24, 2013

(65) Prior Publication Data
US 2015/0133378 A1 May 14, 2015

Related U.S. Application Data (60) Provisional application No. 61/625,636, filed on Apr. 17, 2012.

(51) Int. Cl.
*G01N 33/53* (2006.01)
*A61P 13/12* (2006.01)
*G01N 33/68* (2006.01)
*C07K 14/47* (2006.01)

(52) U.S. Cl.
CPC ..... *G01N 33/5308* (2013.01); *G01N 33/6893* (2013.01); *C07K 14/47* (2013.01); *G01N 2333/775* (2013.01); *G01N 2800/085* (2013.01); *G01N 2800/245* (2013.01); *G01N 2800/50* (2013.01); *G01N 2800/54* (2013.01)

(58) Field of Classification Search
None
See application file for complete search history.

(56) References Cited

U.S. PATENT DOCUMENTS

| 2005/0272649 A1 | 12/2005 | Hruska et al. |
| 2011/0020367 A1 | 1/2011 | Strom et al. |
| 2011/0065608 A1 | 3/2011 | Labrie et al. |
| 2011/0177959 A1 | 7/2011 | Spain et al. |

OTHER PUBLICATIONS

Hidaka et al (2002. Cell Tissue Res. 310: 289-296).*
Metcalfe, 2007. Nephrol Dial Transplant. 22(9): 26-30.*
Cappelletti et al., "Patterns and changes in gene expression following neo-adjuvant anti-estrogen treatment in estrogen receptor-positive breast cancer," Endocrine-Related Cancer, 2008, 15: 439-449.
Cochrane et al., "Differential regulation of clusterin and its isoforms by androgens in prostate cells," Journal of Biological Chemistry, 2007, 282: 2278-2287.
De Beuf et al., "Epoetin delta as an antifibrotic agent in the remnant kidney rat: a possible role for transforming growth factor beta and hepatocyte growth factor," Nephron Exp Nephrol., 2010, 115: e46-e59.
de Silva et al., "Apolipoprotein J: structure and tissue distribution," Biochemistry, 1990, 29: 5380-5389.
Devauchelle et al., "Characterization and functional consequences of underexpression of clusterin in rheumatoid arthritis," J Immunol., 2006, 177: 6471-6479.
Isoniemi et al., "Histological chronic allograft damage index accurately predicts chronic renal allograft rejection," Transplantation, Dec. 1994, 1195-1198.
Jenne and Tschopp, "Molecular structure and functional characterization of a human complement cytolysis inhibitor found in blood and seminal plasma: identity to sulfated glycoprotein 2, a constituent of rat testis fluid," PNAS, 1989, 86: 7123-7127.
'Hitocompatibilityandimmunogenetics.com' [online]. "Histocompatibility & Immunogenetics—a collection of brief revision notes," Aug. 8, 2012, [retrieved on Apr. 17, 2017]. Retrieved from the Internet: URL <http://www.histocompatibilityandimmunogenetics.com/>. 2 pages.
Mallory et al., "A novel group of genes regulates susceptibility to antineoplastic drugs in highly tumorigenic breast cancer cells," Molecular Pharmacology, 2005, 68: 1747-1756.
Miyake et al., "Testosterone-repressed prostate message-2 is an antiapoptotic gene involved in progression to androgen independence in prostate cancer," Cancer Research, 2000, 60: 170-176.
Negri , "Prevention of progressive fibrosis in chronic renal diseases: antifibrotic agents," J Nephrol, 2004, 17: 496-503.
Nuutinen et al., "Clusterin: a forgotten player in Alzheimer's disease," Brain Res Rev, Oct. 2009, 61: 89-104.
Reddy et al., "Transforming Growth Factor β (TGFβ)-Induced Nuclear Localization of Apolipoprotein J/Clusterin in Epithelial Cells," Biochemistry, May 1996, 35: 6157-6163.

(Continued)

*Primary Examiner* — Zachary Howard
(74) *Attorney, Agent, or Firm* — Fish & Richardson P.C.

(57) ABSTRACT

A method for identifying a kidney transplant recipient at an increased risk of developing interstitial fibrosis or tubular atrophy which comprises obtaining a post-transplant urine sample from the kidney transplant recipient; measuring the level of clusterin in the urine sample; comparing the level of clusterin in the patient sample to the level of clusterin in a control sample from the urine of a non-fibrotic kidney transplant recipient; diagnosing a kidney transplant recipient with a clusterin level that is significantly higher than the clusterin level in the control as being at an increased risk of developing interstitial fibrosis or tubular atrophy.

14 Claims, 2 Drawing Sheets

(56) References Cited

OTHER PUBLICATIONS

Redondo et al., "Overexpression of clusterin in human breast carcinoma," American Journal of Pathology, 2000, 157: 393-399.
Rizzi and Bettuzzi, "The Clusterin Paradigm in Prostate and Breast Carcinogenesis," Endocrine-Related Cancer, 2010, 17: R1-R17.
Saverio et al., "Tumor progression is accompanied by significant changes in the levels of expression of polyamine metabolism regulatory genes and clusterin (sulfated glycoprotein 2) in human prostate cancer specimens," Cancer Research, Jan. 2000, 60: 28-34.
Shannan et al., "Challenge and promise: roles for clusterin in pathogenesis, progression and therapy of cancer," Cell Death and Differentiation, 2006, 13: 12-19.
Solez et al., "Banff '05 Meeting Report: Differential Diagnosis of Chronic Allograft Injury and Elimination of Chronic Allograft Nephropathy ('CAN')," American Journal of Transplantation, Mar. 2007, 7: 518-526.
Solez et al., "Banff '07 Classification of Renal Allograft Pathology:Updates and Future Directions," American Journal of Transplantation, Apr. 2008, 753-760.
Wong et al., "Molecular characterization of human TRPM-2/clusterin, a gene associated with sperm maturation, apoptosis and neurodegeneration," European Journal of Biochemistry, 1994, 221: 917-1925.
Zhang et al., "Clusterin inhibits apoptosis by interacting with activated Bax," Nature Cell Biology, Sep. 2005, 909-915.

* cited by examiner

METHOD FOR PREDICTING RISK OF EXPOSURE TO INTERSTITIAL FIBROSIS AND TUBULAR ATROPHY WITH CLUSTERIN

This application claims priority to U.S. Provisional Patent Application Ser. No. 61/625,636, filed on Apr. 17, 2012, which is incorporated in its entirety by reference herein.

GOVERNMENT CLAUSE

This invention was made with government support under AI070107 awarded by The National Institutes of Health. The government has certain rights in the invention.

BACKGROUND OF THE INVENTION

Clusterin (CLU) is a secreted multi-function glycoprotein that has been associated with clearance of debris, apoptosis inhibition, tissue remodeling, complement inhibition, regulation of complement-mediated cell lysis, membrane recycling, cell-cell adhesion and epithelial growth. CLU is a single 9-exon gene expressing three protein forms[1,2,3]. Each of the forms has distinct sub-cellular localizations and biological functions[4,5]; CLU has nearly ubiquitous tissue distribution. Due to functions such as regulatory activity on complement, CLU is involved in inflammation and autoimmunity.

CLU is implicated in a number of disease states including cancer, Alzheimer's disease, and rheumatoid arthritis[6,7,8]. It is overexpressed in several human cancers, and its suppression deems cancer cells sensitive to chemotherapeutic drug-mediated apoptosis[9]. However, despite the many reports on CLU functionality and its relation to tumorigenesis, many contradictions in the data still exist. Understanding the role of CLU in tumorigenesis is complicated not only by the existence of different protein forms but also by the changes of tumors over time and the treatment-induced alterations such as hormone ablation or chemotherapyl[10,11,12]. CLU has been found to be dysregulated in many types of cancer including prostate and breast cancer[13,14,15]. Similarly, CLU was initially shown to be upregulated in Alzheimer's Disease (AD) and later observed to bind to amyloid beta peptides and preclude defibrilization of the amyloid peptides. Amongst its numerous functions in the brain, CLU aids in the clearance of amyloid-beta peptides and fibrils by binding to megalin receptors to enhance their endocytosis within glial cells[7]. Further, CLU is also present in lipoprotein particles and hence regulates cholesterol and lipid metabolism, which is compromised in the brains of AD patients[7].

Chronic allograft nephropathy (CAN) (chronic allograft injury/rejection) is of great concern in long term renal allograft survival. CAN differs from 'chronic rejection' in that it is an end point of tubular atrophy and interstitial fibrosis (IF/TA) in the graft caused by a series of immune and non-immune insults to the kidney, leading ultimately to graft failure.

Interstitial fibrosis is considered to be present when the supporting connective tissue in the renal parenchyma exceeds 5% of the cortical area.

Tubular atrophy refers to the presence of tubules with thick redundant basement membranes, or a reduction of greater than 50% in tubular diameter compared to surrounding non-atrophic tubules. IF/TA is contributed to by pre-existing donor factors such as donor age, underlying disease or donor-recipient size disparity; by immune factors involving acute and chronic humoral and cellular processes; or by post-transplant factors including drug toxicity and infection. A number of immune mechanisms contribute to CAN including acute and chronic alloantibody-mediated rejection as well as acute and chronic cellular rejection. The consequences of antibody mediated processes are a distinct set of histological features, mainly Transplant Glomerulopathy (TG), which is characterized by a doubling of the glomerular basement membrane (GBM), which is usually accompanied by IF/TA. Recurrent late acute cellular or antibody mediated rejection which is resistant to treatment is a critical predictor of CAN development.

What is needed in the art are markers whose expression can be used to identify patients suffering from kidney diseases and predict the development of kidney fibrosis. In addition, such markers are needed to identify renal allograft recipients who are at risk for developing IF/TA and represent targets for therapeutic intervention to prevent the development of IF/TA at an early stage, thereby preventing the development of CAN.

SUMMARY OF THE INVENTION

The present invention is based on the discovery that a specific urine biomarker, Clusterin, is predictive of poor graft function and chronic allograft dysfunction and for increased risk of developing IF/TA.

In one aspect, the present invention provides a method for identifying a kidney transplant recipient at an increased risk of developing fibrosis which comprise obtaining a post-transplant urine sample from the kidney transplant recipient; measuring the level of clusterin in the urine sample; comparing the level of clusterin in the patient sample to the level of clusterin in a control sample from the urine of a non-fibrotic kidney transplant recipient; and diagnosing a patient with a clusterin level that is significantly higher than the clusterin level in the control as being at an increased risk of developing interstitial fibrosis.

In another aspect, the present invention provides a method for identifying a kidney transplant recipient at an increased risk of developing tubular atrophy which comprises obtaining a post-transplant urine sample from the kidney transplant recipient; measuring the level of clusterin in the urine sample; comparing the level of clusterin in the patient sample to the level of clusterin in a control sample from the urine of a kidney transplant recipient that is not afflicted with tubular atrophy; and diagnosing a patient with a clusterin level that is significantly higher than the clusterin level in the control as being at an increased risk of developing tubular atrophy.

In a further aspect, the present invention provides a method for identifying a patient at increased risk of developing decreased renal function in a kidney transplant recipient which comprises the steps of obtaining a post-transplant urine sample from the patient; measuring the level of clusterin in the urine sample from the patient; comparing the level of clusterin in the sample to the level of clusterin in a control urine sample obtained from a non-fibrotic kidney transplant recipient; and diagnosing the patient as being at an increased risk of developing decreased renal function if the clusterin level in the patient's urine sample is more than 50% higher than the clusterin level in the control.

In yet a further aspect, the present invention provides a method for identifying a patient at increased risk of developing interstitial fibrosis or tubular atrophy which comprises the steps of obtaining a urine sample from the patient; measuring the level of clusterin in the urine sample; comparing the level of clusterin in the sample to the level of clusterin in a control urine sample from an individual not afflicted with interstitial fibrosis or tubular atrophy; and diagnosing the patient with a clusterin level that is significantly higher than the clusterin level in the control as being at an increased risk of developing tubular atrophy or interstitial fibrosis.

In yet a further aspect, the present invention provides a method for identifying a patient at increased risk of developing interstitial fibrosis or tubular atrophy which comprises the steps of obtaining a urine sample from the patient; measuring the level of clusterin in the urine sample; comparing the level of clusterin in the sample to the level of clusterin in a control urine sample from an individual not afflicted with interstitial fibrosis or tubular atrophy; and diagnosing the patient with a clusterin level that is at least 50% higher, and preferably 100% higher, than the clusterin level in the control as being at an increased risk of developing tubular atrophy or interstitial fibrosis.

In a still further aspect of the present invention the patient diagnosed as being at-risk for IF/TA is treated for interstitial fibrosis and/or tubular atrophy.

These and other aspects of the present invention will be apparent to those of ordinary skill in the art in light of the present description, claims and drawings.

DETAILED DESCRIPTION OF THE INVENTION

Definitions

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude), preferably within a factor of two of a given value.

The term "significantly higher levels of Clusterin" is defined herein as at least 50%, and preferably 100% higher than in the control.

The present invention is based on the unexpected discovery that the levels of Clusterin in the urine of a kidney allograft recipient are significantly higher when compared to control urine samples obtained from kidney allograft recipient's urine who is not suffering from IF/TA. This is unexpected because before the present invention no such function had been ascribed to Clusterin.

The Clusterin protein (SEQ ID NOs: 1-5) found in the urine has now been identified as a member of a gene expression signature, which is predictive of IF/TA and decreased renal function in kidney recipients. Following urine collection and analysis at both 3 and 6 months post kidney transplant, a renal biopsy was performed at 1 year, the pathology read as per the Banff protocol[18,19] and compared to the analysis. The Banff classification 1 characterizes five categories of renal allograft pathology: (1) antibody-mediated rejection; (2) suspicious of acute rejection; (3) acute rejection; (4) chronic sclerosing allograft nephropathy; and (5) other—changes not considered due to rejection.

It was observed that a higher urine Clusterin level at 3 and 6 months correlated with increased instances of IF/TA at the 12 month protocol biopsy. Similarly, lower urine Clusterin levels at 3 and 6 months were noted in patients with normal histology at 12 months.

Pursuant to the present invention Clusterin levels are measured in the urine of a kidney graft recipient. Preferably, soluble concentrations of clusterin in the patient's urine are assayed using a commercially available sandwich ELISA kit (Human Clusterin immunoassay, DCLUOO, R&D systems, UK) according to the manufacturer's instructions. In another embodiment, clusterin levels are measured in the urine of a patient believed to be at risk for IF/TA.

The clusterin level of the patient (transplant recipient or at-risk for IF/TA) is measured and compared to the clusterin level of a standard control (patient not afflicted with IF/TA). If the patient's measured clusterin level is significantly higher (at least 50% or more) than the control, the patient is diagnosed as being at-risk for IF/TA. The patient is then treated for interstitial fibrosis or tubular atrophy.

Further, renal function at 12 months also correlated with the 3- and 6-month Clusterin observation. Lower estimated glomarular filtration rate (eGFR), a measure of renal function, was noted in patients at 12 months who had significantly higher urinary Clusterin levels at 3 and 6 months. The results were consistent among various age, gender, transplant type and Delayed Graft Function (DGF) groups.

A patient identified as likely to develop fibrosis at the 12-month mark based on the 3-month Clusterin profile would provoke the necessary clinical steps required to inhibit or decrease progression of fibrosis development. In one embodiment, calcineurin inhibitors (CNIs), such as cyclosporine or tacrolimus, or a less fibrogenic immunosuppressive drug such as mycophenolate mofetil (MMF) or sirolimus, can be employed. In another embodiment, anti-fibrotic agents such as Pirfenidone (Esbriet), Relaxin, Bone morphogenetic protein 7 (BMP-7), Hepatocyte growth factor (HGF), or Epoetin delta can be administered to the patients identified as having elevated clusterin levels and increased risk of exposure to IF/TA[20,21].

Since patients who are identified as being at risk for developing IF/TA have impaired renal function and often suffer from hypertension, administration of an angiotensin converting enzyme inhibitor (ACEI) such as lisinopril or angiotensin II receptor antagonists such as losartan, to such patients is within the scope of the present invention.

In one embodiment of the invention, renal transplant patients are tested for the level of Clusterin in their urine at 3 months and 6 months post-transplant. The patient's Clusterin protein level is compared to a standard Clusterin level based on samples from renal transplant recipients that do not suffer from IF/TA. Patients identified as having Clusterin levels that are significantly higher (as defined above) than those in the Clusterin standard, are at increased risk of developing IF/TA and should receive appropriate treatment including, for example, anti-fibrotic agents.

The present invention is described below in working examples which are intended to further describe the invention without limiting the scope thereof.

In the Examples below the following materials and methods were used.

All kidney transplant recipients had anti-IL-2R mAb induction with Tacrolimus, mycophenolate, and prednisolone to maintain immune-suppression. This was the immunosuppression regimen for the patients that had Clusterin measured in the urine.

mRNA expression was determined by microarray on 160 biopsies of a 3-month protocol. The biopsies were performed for study purposes only to show a lack of renal dysfunction at the time. Utilizing the samples collected at 3 months, specific genes were determined to be associated with an increased CADI, an established measure of fibrosis which uses components of the BANFF score for renal transplant biopsies, and a decreased estimated Glomalular Filtration Rate (eGFR) at 1 year. Estimated GFR is based on creatinine and is a measure of renal function. Ninety-four biopsies with the 1-year endpoints were analyzed.

Example 1

Clusterin was observed to be highly associated with the development of fibrosis and the decline of renal function at the 12-month time point. Expression of Clusterin in the biopsy was not associated with fibrosis at the time of the 3-month biopsy but was associated with eGFR.

Clusterin was then measured in the urine. Soluble concentrations of Clusterin in the patient's urine were assayed using a commercially available sandwich ELISA kit (Human Clusterin immunoassay, DCLUOO, R&D systems, UK) according to the manufacturer's instructions. All urine samples were prepared at a 4-fold dilution and were run in duplicate. After the development of the colorimetric reaction, the OD at 450 nm was quantified by an eight-channel spectrophotometer, and the OD readings were converted to nanograms per milliliter (ng/ml) on the basis of the standard curves obtained with human Clusterin standard preparations. Clusterin concentrations were represented as "mean±SD".

Figure 1:
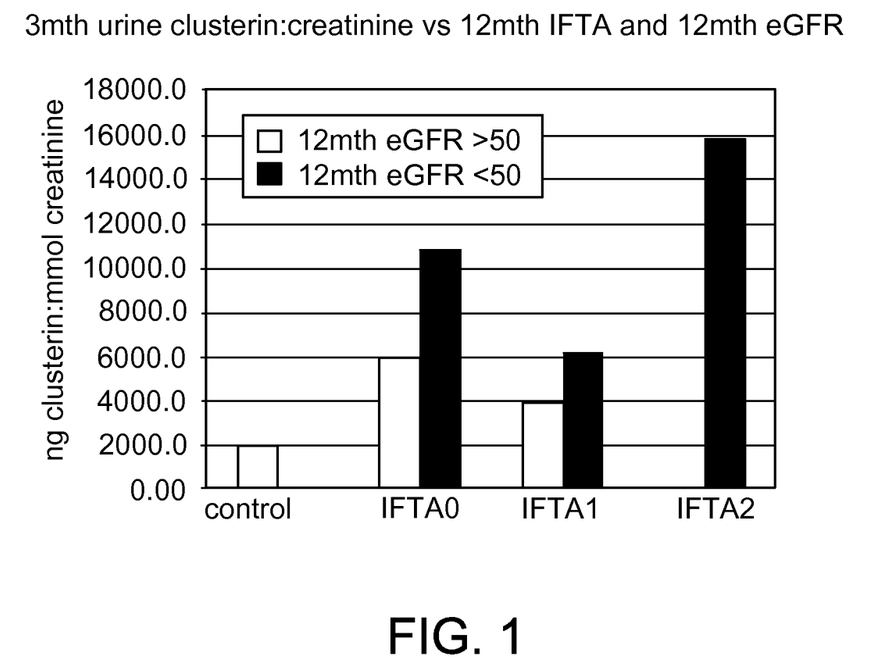
FIG. 1 is a graph comparing 3 month urine clusterin:creatinine concentrations vs 12 month IF/TA and 12 month eGFR. IF/TA 0, 1 and 2 correspond to no, mild, or moderate severity of fibrosis, respectively.

The assay was done initially in 18 patients with 3-month urine and 12-month endpoint data (see FIG. 1). In addition, the data was analyzed from 29 renal transplant patients and utilized urine from different time points and at different levels of renal function to observe any correlation between the time post-transplant and renal function.

Concentrations of proteins in the urine can vary depending on how concentrated the urine sample is; hence, urinary Custerin levels were normalized to creatinine in each sample. As shown in FIG. 1, increased concentration of Clusterin measured at 3 months correlated with higher instances of decreased renal function as noted by <50 (mL/min) of eGFR at the 12-month biopsy analysis. Further, higher instances of decreased renal function correlated with increased severity of IF/TA. In FIG. 1, IF/TA 0, 1 and 2 correspond to no, mild, or moderate severity of fibrosis, respectively.

Figure 2:
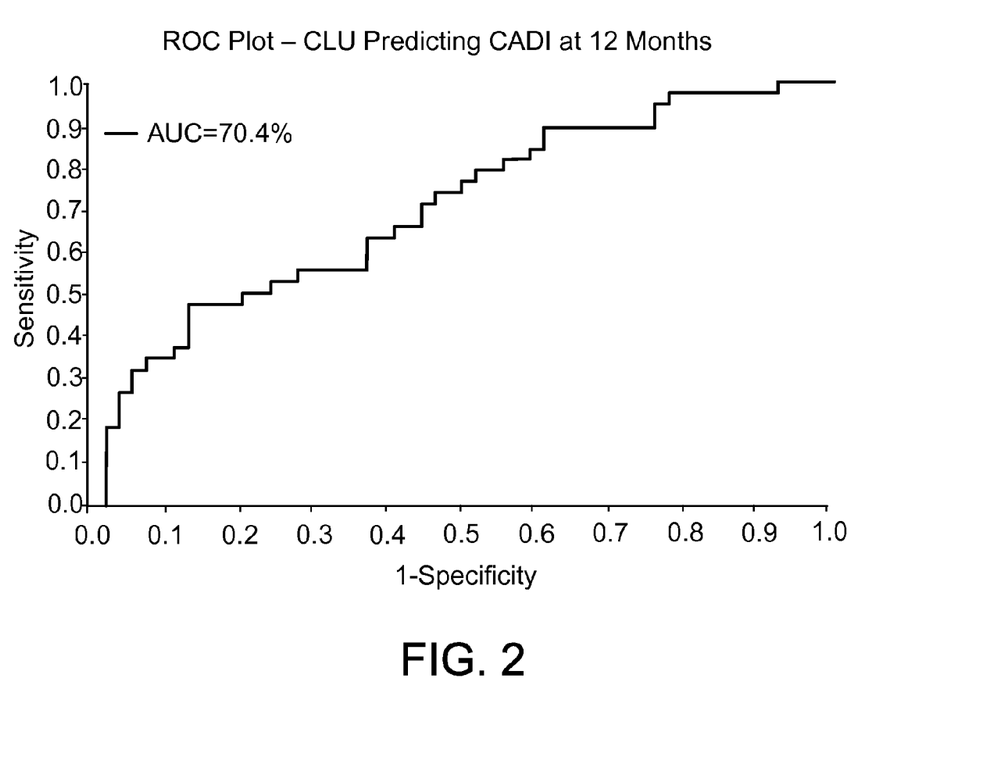
FIG. 2 is a graph displaying the ROC (Receiver Operating Characteristic) for the prediction of CADI (Chronic Allograft Damage Index) by intragraft mRNA expression. This is based on the microarray expression data.

FIG. 2 displays the ROC (Receiver Operating Characteristic) for the prediction of CADI (Chronic Allograft Damage Index) by intragraft mRNA expression. This is based on the microarray expression data. In FIG. 2, Sensitivity (y-axis) and Specificity (x-axis) are statistical measures of the performances of a binary classification test, also known in statistics as classification function. Sensitivity (also referred to as a "recall rate" in certain fields) measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). A perfect predictor would be described as having 100% specificity (i.e. not predicting anyone from the healthy group as sick); however all predictors have some error.

$$\text{Sensitivity} = \frac{\text{Number of true positives}}{\text{Number of true positives} + \text{number of false negatives}} =$$

probability of a positive test given that the patient is ill $$\text{Specificity} = \frac{\text{Number of true negatives}}{\text{Number of true negatives} + \text{number of false positives}} =$$

probability of a positive test given that the patient is well

Presented below in Tables 1 and 2 are the raw RNA data that is used to determine correlation with CADI.

TABLE 1

| Diagnostic Test | eGFR | CLU |
| --- | --- | --- |
| AUC | 67.8% | 70.4% |
| Optimal Cut-Off Point | 9.0371 | 9.0457 |
| Sensitivity | 0.50 | 0.47 |
| Specificity | 0.22 | 0.87 |
| NPV | 0.39 | 0.70 |
| PPV | 0.31 | 0.72 |

Table 1 shows that intragraft expression of Clusterin is a more accurate predictor of fibrosis at the 12-month mark than the current standard of creatinine at 3 months. It compares urinary Clusterin at 3 months as a predictor of CADI as compared to eGFR at 3 months as a predictor of fibrosis at 3 months. As can be seen in Table 1, Clusterin had a higher Specificity (87%) than eGFR (22%).

Overall, Table 1 shows a correlation between Clusterin levels and eGFR.

eGFR is positive if eGFR<40 otherwise negative

CADI is positive if CADI>2 otherwise negative

TABLE 2

| Diagnostic Test | eGFR 12 Month Clu | CADI 12 Month Clu |
| --- | --- | --- |
| AUC | 69.3% | 70.4% |
| Optimal Cut-Off Point | 9.0371 | 9.0457 |
| Sensitivity | 0.68 | 0.47 |
| Specificity | 0.70 | 0.87 |
| NPV | 0.93 | 0.70 |
| PPV | 0.28 | 0.72 |

Currently eGFR (e.g. creatinine) is used as a predictor of CADI at 12 months (see below). Clusterin is a more specific predictor of CADI at 12 months than eGFR as a predictor of CADI.

The AUC is 67.8%.

Optimal Cutpoint is 50.37

Sensitivity: 0.50

Specificity: 0.22

PPV: 0.31

NPV: 0.39

Presented below are the amino acid sequences of Clusterin isoforms 1-5 (SEQ ID NOS:1-5)

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

REFERENCES

1. Wong P, Taillefer D, Lakins J, Pineault J, Chader G & Tenniswood M. 1994. Molecular characterization of human TRPM-2/clusterin, a gene associated with sperm maturation, apoptosis and neurodegeneration. European Journal of Biochemistry 221917-925
2. Jenne D E & Tschopp J. 1989. Molecular structure and functional characterization of a human complement cytolysis inhibitor found in blood and seminal plasma: identity to sulfated glycoprotein 2, a constituent of rat testis fluid. PNAS 867123-7127.
3. Cochrane D R, Wang Z, Muramaki M, Gleave M E & Nelson C C. 2007. Differential regulation of clusterin and its isoforms by androgens in prostate cells. Journal of Biological Chemistry 2822278-2287.
4. de Silva H V, Harmony J A, Stuart W D, Gil C M & Robbins J. 1990a. Apolipoprotein J: structure and tissue distribution. Biochemistry 295380-5389.
5. Reddy K B, Jin G, Karode M C, Harmony J A & Howe P H. 1996. Transforming growth factor beta (TGF beta)-induced nuclear localization of Apolipoprotein J/clusterin in epithelial cells. Biochemistry 356157-6163.
6. Shannan B, Seifert M, Leskov K, Willis J, Booth man D, Tilgen W & Reichrath J. 2006. Challenge and promise: roles for clusterin in pathogenesis, progression and therapy of cancer. Cell Death and Differentiation 1312-19.
7. Nuutinen T, Suuronen T, Kauppinen A, Salminen A. 2009. Clusterin: a forgotten player in Alzheimer's disease. Brain Res Rev:89-104.
8. Devauchelle V, Essabbani A, De Pinieux G, Germain S, Tourneur L, Mistou S, Margottin-Goguet F, Anract P, Migaud H, Le Nen D, Lequerré T, Saraux A, Dougados M, Breban M, Fournier C, Chiocchia G. 2006. Characterization and functional consequences of underexpression of clusterin in rheumatoid arthritis. J Immunol. 6471-9.
9. Zhang, H, Kim, J, Edwards, C, Xu, Z, Taichman, R and Wang, C. 2005. Clusterin inhibits apoptosis by interacting with activated Bax. Nature Cell Biology 909-915.
10. Miyake H, Nelson C, Rennie P, and Gleave M E. 2000b. Testosterone-repressed prostate message-2 is an antiapoptotic gene involved in progression to androgen independence in prostate cancer. Cancer Research 60170-176.
11. Mallory J C, Crudden G, Oliva A, Saunders C, Stromberg A and Craven R J. 2005. A novel group of genes regulates susceptibility to antineoplastic drugs in highly tumorigenic breast cancer cells. Molecular Pharmacology 681747-1756.
12. Cappelletti V, Gariboldi M, De Cecco L, Toffanin S, Reid J F, Lusa L, Bajetta E, Celio L, Greco M, Fabbri A et al. 2008. Patterns and changes in gene expression following neo-adjuvant anti-estrogen treatment in estrogen receptor-positive breast cancer. Endocrine-Related Cancer 15439-449.
13. Redondo M, Villar E, Torres-Munoz J, Tellez T, Morell M & Petito C K. 2000. Overexpression of clusterin in human breast carcinoma. American Journal of Pathology 157393-399.
14. Bettuzzi S, Davalli P, Astancolle S, Carani C, Madeo B, Tampieri A and Corti A. 2000. Tumor progression is accompanied by significant changes in the levels of expression of polyamine metabolism regulatory genes and clusterin (sulfated glycoprotein 2) in human prostate cancer specimens. Cancer Research 6028-34.
15. Rizzi, F and Bettuzzi, S. 2010. The Clusterin Paradigm in Prostate and Breast Carcinogenesis. Endocrine-Related Cancer R1-R17.
16. Kallon, Delordson. Histocompatibility & Immunogenetics—a collection of brief revision notes. http://www.histocompatibilityandimmunogenetics.com/17.
17. K. Solez, R. B. Colvin, L. C. Racusen, B. Sis, P. F. Halloran, P. E. Birk, P. M. Campbell, M. Cascalho, A. B. Collins, A. J. et al. 2007. Chronic Allograft Injury and Elimination of Chronic Allograft Nephropathy: Chronic Alloimmune Injury/Rejection versus Non-Immune Injury. American Journal of Transplantation. 2007 518-526.
18. Isoniemi H, Taskinen E, Hayry P. 1994 Histological chronic allograft damage index accurately predicts chronic renal allograft rejection. Transplantation 1195-8.
19. Solez et al. 2008. Banff 07 Classification of Renal Allograft Pathology: Updates and Future Directions. American Journal of Transplantation 753-760.
20. Negri, A L. 2004. Prevention of progressive fibrosis in chronic renal diseases: antifibrotic agents. J Nephrol. 496-503.
21. De Beuf A, D'Haese P C, Verhulst A. 2010. Epoetin delta as an antifibrotic agent in the remnant kidney rat: a possible role for transforming growth factor beta and hepatocyte growth factor. Nephron Exp Nephrol. e46-59

SEQUENCE LISTING

```
<160> NUMBER OF SEQ ID NOS: 5

<210> SEQ ID NO 1
<211> LENGTH: 449
<212> TYPE: PRT
<213> ORGANISM: Homo sapiens

<400> SEQUENCE: 1

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
```

```
                35                  40                  45
Ala Val Asn Gly Val Lys Gln Ile Lys Thr Leu Ile Glu Lys Thr Asn
    50                  55                  60
Glu Glu Arg Lys Thr Leu Leu Ser Asn Leu Glu Ala Lys Lys Lys
65                  70                  75                  80
Lys Glu Asp Ala Leu Asn Glu Thr Arg Glu Ser Glu Thr Lys Leu Lys
                85                  90                  95
Glu Leu Pro Gly Val Cys Asn Glu Thr Met Met Ala Leu Trp Glu Glu
            100                 105                 110
Cys Lys Pro Cys Leu Lys Gln Thr Cys Met Lys Phe Tyr Ala Arg Val
            115                 120                 125
Cys Arg Ser Gly Ser Gly Leu Val Gly Arg Gln Leu Glu Glu Phe Leu
            130                 135                 140
Asn Gln Ser Ser Pro Phe Tyr Phe Trp Met Asn Gly Asp Arg Ile Asp
145                 150                 155                 160
Ser Leu Leu Glu Asn Asp Arg Gln Gln Thr His Met Leu Asp Val Met
                165                 170                 175
Gln Asp His Phe Ser Arg Ala Ser Ser Ile Ile Asp Glu Leu Phe Gln
            180                 185                 190
Asp Arg Phe Phe Thr Arg Glu Pro Gln Asp Thr Tyr His Tyr Leu Pro
            195                 200                 205
Phe Ser Leu Pro His Arg Arg Pro His Phe Phe Pro Lys Ser Arg
210                 215                 220
Ile Val Arg Ser Leu Met Pro Phe Ser Pro Tyr Glu Pro Leu Asn Phe
225                 230                 235                 240
His Ala Met Phe Gln Pro Phe Leu Glu Met Ile His Glu Ala Gln Gln
                245                 250                 255
Ala Met Asp Ile His Phe His Ser Pro Ala Phe Gln His Pro Pro Thr
            260                 265                 270
Glu Phe Ile Arg Glu Gly Asp Asp Arg Thr Val Cys Arg Glu Ile
            275                 280                 285
Arg His Asn Ser Thr Gly Cys Leu Arg Met Lys Asp Gln Cys Asp Lys
290                 295                 300
Cys Arg Glu Ile Leu Ser Val Asp Cys Ser Thr Asn Asn Pro Ser Gln
305                 310                 315                 320
Ala Lys Leu Arg Arg Glu Leu Asp Glu Ser Leu Gln Val Ala Glu Arg
                325                 330                 335
Leu Thr Arg Lys Tyr Asn Glu Leu Leu Lys Ser Tyr Gln Trp Lys Met
            340                 345                 350
Leu Asn Thr Ser Ser Leu Leu Glu Gln Leu Asn Glu Gln Phe Asn Trp
            355                 360                 365
Val Ser Arg Leu Ala Asn Leu Thr Gln Gly Glu Asp Gln Tyr Tyr Leu
            370                 375                 380
Arg Val Thr Thr Val Ala Ser His Thr Ser Asp Ser Asp Val Pro Ser
385                 390                 395                 400
Gly Val Thr Glu Val Val Lys Leu Phe Asp Ser Asp Pro Ile Thr
                405                 410                 415
Val Thr Val Pro Val Glu Val Ser Arg Lys Asn Pro Lys Phe Met Glu
            420                 425                 430
Thr Val Ala Glu Lys Ala Leu Gln Glu Tyr Arg Lys Lys His Arg Glu
            435                 440                 445
Glu
```

<210> SEQ ID NO 2
<211> LENGTH: 501
<212> TYPE: PRT
<213> ORGANISM: Homo sapiens

<400> SEQUENCE: 2

Met Gln Val Cys Ser Gln Pro Gln Arg Gly Cys Val Arg Glu Gln Ser
 1               5                  10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
    50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

Glu Leu Phe Gln Asp Arg Phe Phe Thr Arg Glu Pro Gln Asp Thr Tyr
                245                 250                 255

His Tyr Leu Pro Phe Ser Leu Pro His Arg Arg Pro His Phe Phe Phe
            260                 265                 270

Pro Lys Ser Arg Ile Val Arg Ser Leu Met Pro Phe Ser Pro Tyr Glu
        275                 280                 285

Pro Leu Asn Phe His Ala Met Phe Gln Pro Phe Leu Glu Met Ile His
    290                 295                 300

Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Arg Thr Val
                325                 330                 335

Cys Arg Glu Ile Arg His Asn Ser Thr Gly Cys Leu Arg Met Lys Asp
            340                 345                 350

Gln Cys Asp Lys Cys Arg Glu Ile Leu Ser Val Asp Cys Ser Thr Asn
        355                 360                 365

Asn Pro Ser Gln Ala Lys Leu Arg Arg Glu Leu Asp Glu Ser Leu Gln
    370                 375                 380

Val Ala Glu Arg Leu Thr Arg Lys Tyr Asn Glu Leu Leu Lys Ser Tyr
385                 390                 395                 400

Gln Trp Lys Met Leu Asn Thr Ser Ser Leu Glu Gln Leu Asn Glu
            405                 410                 415

Gln Phe Asn Trp Val Ser Arg Leu Ala Asn Leu Thr Gln Gly Glu Asp
            420                 425                 430

Gln Tyr Tyr Leu Arg Val Thr Thr Val Ala Ser His Thr Ser Asp Ser
        435                 440                 445

Asp Val Pro Ser Gly Val Thr Glu Val Val Val Lys Leu Phe Asp Ser
        450                 455                 460

Asp Pro Ile Thr Val Thr Val Pro Val Glu Val Ser Arg Lys Asn Pro
465                 470                 475                 480

Lys Phe Met Glu Thr Val Ala Glu Lys Ala Leu Gln Glu Tyr Arg Lys
                485                 490                 495

Lys His Arg Glu Glu
            500

<210> SEQ ID NO 3
<211> LENGTH: 274
<212> TYPE: PRT
<213> ORGANISM: Homo sapiens

<400> SEQUENCE: 3

Met Gln Asp His Phe Ser Arg Ala Ser Ser Ile Ile Asp Glu Leu Phe
1               5                   10                  15

Gln Asp Arg Phe Phe Thr Arg Glu Pro Gln Asp Thr Tyr His Tyr Leu
            20                  25                  30

Pro Phe Ser Leu Pro His Arg Arg Pro His Phe Phe Phe Pro Lys Ser
        35                  40                  45

Arg Ile Val Arg Ser Leu Met Pro Phe Ser Pro Tyr Glu Pro Leu Asn
    50                  55                  60

Phe His Ala Met Phe Gln Pro Phe Leu Glu Met Ile His Glu Ala Gln
65                  70                  75                  80

Gln Ala Met Asp Ile His Phe His Ser Pro Ala Phe Gln His Pro Pro
                85                  90                  95

Thr Glu Phe Ile Arg Glu Gly Asp Asp Arg Thr Val Cys Arg Glu
            100                 105                 110

Ile Arg His Asn Ser Thr Gly Cys Leu Arg Met Lys Asp Gln Cys Asp
        115                 120                 125

Lys Cys Arg Glu Ile Leu Ser Val Asp Cys Ser Thr Asn Asn Pro Ser
130                 135                 140

Gln Ala Lys Leu Arg Arg Glu Leu Asp Glu Ser Leu Gln Val Ala Glu
145                 150                 155                 160

Arg Leu Thr Arg Lys Tyr Asn Glu Leu Leu Lys Ser Tyr Gln Trp Lys
                165                 170                 175

Met Leu Asn Thr Ser Ser Leu Glu Gln Leu Asn Glu Gln Phe Asn
            180                 185                 190

Trp Val Ser Arg Leu Ala Asn Leu Thr Gln Gly Glu Asp Gln Tyr Tyr
        195                 200                 205

Leu Arg Val Thr Thr Val Ala Ser His Thr Ser Asp Ser Asp Val Pro
    210                 215                 220

Ser Gly Val Thr Glu Val Val Val Lys Leu Phe Asp Ser Asp Pro Ile
225                 230                 235                 240

Thr Val Thr Val Pro Val Glu Val Ser Arg Lys Asn Pro Lys Phe Met

```
                        245                 250                 255
Glu Thr Val Ala Glu Lys Ala Leu Gln Glu Tyr Arg Lys Lys His Arg
                260                 265                 270

Glu Glu

<210> SEQ ID NO 4
<211> LENGTH: 416
<212> TYPE: PRT
<213> ORGANISM: Homo sapiens

<400> SEQUENCE: 4

Met Ser Asn Gln Gly Ser Lys Tyr Val Asn Lys Glu Ile Gln Asn Ala
  1               5                  10                  15

Val Asn Gly Val Lys Gln Ile Lys Thr Leu Ile Glu Lys Thr Asn Glu
                 20                  25                  30

Glu Arg Lys Thr Leu Leu Ser Asn Leu Glu Glu Ala Lys Lys Lys Lys
             35                  40                  45

Glu Asp Ala Leu Asn Glu Thr Arg Glu Ser Glu Thr Lys Leu Lys Glu
         50                  55                  60

Leu Pro Gly Val Cys Asn Glu Thr Met Met Ala Leu Trp Glu Glu Cys
 65                  70                  75                  80

Lys Pro Cys Leu Lys Gln Thr Cys Met Lys Phe Tyr Ala Arg Val Cys
                 85                  90                  95

Arg Ser Gly Ser Gly Leu Val Gly Arg Gln Leu Glu Glu Phe Leu Asn
                100                 105                 110

Gln Ser Ser Pro Phe Tyr Phe Trp Met Asn Gly Asp Arg Ile Asp Ser
            115                 120                 125

Leu Leu Glu Asn Asp Arg Gln Gln Thr His Met Leu Asp Val Met Gln
        130                 135                 140

Asp His Phe Ser Arg Ala Ser Ser Ile Ile Asp Glu Leu Phe Gln Asp
145                 150                 155                 160

Arg Phe Phe Thr Arg Glu Pro Gln Asp Thr Tyr His Tyr Leu Pro Phe
                165                 170                 175

Ser Leu Pro His Arg Arg Pro His Phe Phe Pro Lys Ser Arg Ile
            180                 185                 190

Val Arg Ser Leu Met Pro Phe Ser Pro Tyr Glu Pro Leu Asn Phe His
        195                 200                 205

Ala Met Phe Gln Pro Phe Leu Glu Met Ile His Glu Ala Gln Gln Ala
    210                 215                 220

Met Asp Ile His Phe His Ser Pro Ala Phe Gln His Pro Pro Thr Glu
225                 230                 235                 240

Phe Ile Arg Glu Gly Asp Asp Arg Thr Val Cys Arg Glu Ile Arg
                245                 250                 255

His Asn Ser Thr Gly Cys Leu Arg Met Lys Asp Gln Cys Asp Lys Cys
            260                 265                 270

Arg Glu Ile Leu Ser Val Asp Cys Ser Thr Asn Pro Ser Gln Ala
        275                 280                 285

Lys Leu Arg Arg Glu Leu Asp Glu Ser Leu Gln Val Ala Glu Arg Leu
    290                 295                 300

Thr Arg Lys Tyr Asn Glu Leu Leu Lys Ser Tyr Gln Trp Lys Met Leu
305                 310                 315                 320

Asn Thr Ser Ser Leu Leu Glu Gln Leu Asn Glu Gln Phe Asn Trp Val
                325                 330                 335

Ser Arg Leu Ala Asn Leu Thr Gln Gly Glu Asp Gln Tyr Tyr Leu Arg
```

```
            340                 345                 350
Val Thr Thr Val Ala Ser His Thr Ser Asp Ser Asp Val Pro Ser Gly
            355                 360                 365

Val Thr Glu Val Val Lys Leu Phe Asp Ser Asp Pro Ile Thr Val
    370                 375                 380

Thr Val Pro Val Glu Val Ser Arg Lys Asn Pro Lys Phe Met Glu Thr
385                 390                 395                 400

Val Ala Glu Lys Ala Leu Gln Glu Tyr Arg Lys Lys His Arg Glu Glu
                405                 410                 415

<210> SEQ ID NO 5
<211> LENGTH: 460
<212> TYPE: PRT
<213> ORGANISM: Homo sapiens

<400> SEQUENCE: 5

Met Glu Ala Cys Lys Asp Ser Arg Ile Gly Gly Met Met Lys Thr Leu
1               5                   10                  15

Leu Leu Phe Val Gly Leu Leu Leu Thr Trp Glu Ser Gly Gln Val Leu
                20                  25                  30

Gly Asp Gln Thr Val Ser Asp Asn Glu Leu Gln Glu Met Ser Asn Gln
            35                  40                  45

Gly Ser Lys Tyr Val Asn Lys Glu Ile Gln Asn Ala Val Asn Gly Val
    50                  55                  60

Lys Gln Ile Lys Thr Leu Ile Glu Lys Thr Asn Glu Glu Arg Lys Thr
65                  70                  75                  80

Leu Leu Ser Asn Leu Glu Glu Ala Lys Lys Lys Lys Glu Asp Ala Leu
                85                  90                  95

Asn Glu Thr Arg Glu Ser Glu Thr Lys Leu Lys Glu Leu Pro Gly Val
            100                 105                 110

Cys Asn Glu Thr Met Met Ala Leu Trp Glu Glu Cys Lys Pro Cys Leu
    115                 120                 125

Lys Gln Thr Cys Met Lys Phe Tyr Ala Arg Val Cys Arg Ser Gly Ser
130                 135                 140

Gly Leu Val Gly Arg Gln Leu Glu Glu Phe Leu Asn Gln Ser Ser Pro
145                 150                 155                 160

Phe Tyr Phe Trp Met Asn Gly Asp Arg Ile Asp Ser Leu Leu Glu Asn
                165                 170                 175

Asp Arg Gln Gln Thr His Met Leu Asp Val Met Gln Asp His Phe Ser
            180                 185                 190

Arg Ala Ser Ser Ile Ile Asp Glu Leu Phe Gln Asp Arg Phe Phe Thr
    195                 200                 205

Arg Glu Pro Gln Asp Thr Tyr His Tyr Leu Pro Phe Ser Leu Pro His
210                 215                 220

Arg Arg Pro His Phe Phe Phe Pro Lys Ser Arg Ile Val Arg Ser Leu
225                 230                 235                 240

Met Pro Phe Ser Pro Tyr Glu Pro Leu Asn Phe His Ala Met Phe Gln
                245                 250                 255

Pro Phe Leu Glu Met Ile His Glu Ala Gln Gln Ala Met Asp Ile His
            260                 265                 270

Phe His Ser Pro Ala Phe Gln His Pro Pro Thr Glu Phe Ile Arg Glu
    275                 280                 285

Gly Asp Asp Asp Arg Thr Val Cys Arg Glu Ile Arg His Asn Ser Thr
290                 295                 300
```

-continued

| | | | | | | | | | | | | | | |
|---|---|---|---|---|---|---|---|---|---|---|---|---|---|---|
| Gly<br>305 | Cys | Leu | Arg | Met<br>310 | Lys | Asp | Gln | Cys | Asp<br>315 | Lys | Cys | Arg | Glu | Ile | Leu<br>320 |
| Ser | Val | Asp | Cys | Ser<br>325 | Thr | Asn | Asn | Pro | Ser<br>330 | Gln | Ala | Lys | Leu | Arg<br>335 | Arg |
| Glu | Leu | Asp | Glu<br>340 | Ser | Leu | Gln | Val | Ala<br>345 | Glu | Arg | Leu | Thr | Arg<br>350 | Lys | Tyr |
| Asn | Glu | Leu<br>355 | Leu | Lys | Ser | Tyr | Gln<br>360 | Trp | Lys | Met | Leu | Asn<br>365 | Thr | Ser | Ser |
| Leu | Leu<br>370 | Glu | Gln | Leu | Asn | Glu<br>375 | Gln | Phe | Asn | Trp | Val<br>380 | Ser | Arg | Leu | Ala |
| Asn<br>385 | Leu | Thr | Gln | Gly | Glu<br>390 | Asp | Gln | Tyr | Tyr | Leu<br>395 | Arg | Val | Thr | Thr | Val<br>400 |
| Ala | Ser | His | Thr | Ser<br>405 | Asp | Ser | Asp | Val | Pro<br>410 | Ser | Gly | Val | Thr | Glu<br>415 | Val |
| Val | Val | Lys | Leu<br>420 | Phe | Asp | Ser | Asp | Pro<br>425 | Ile | Thr | Val | Thr | Val<br>430 | Pro | Val |
| Glu | Val | Ser<br>435 | Arg | Lys | Asn | Pro | Lys<br>440 | Phe | Met | Glu | Thr | Val<br>445 | Ala | Glu | Lys |
| Ala | Leu<br>450 | Gln | Glu | Tyr | Arg | Lys<br>455 | Lys | His | Arg | Glu | Glu<br>460 | | | | |

What is claimed is:

1. A method for treating a kidney transplant recipient at an increased risk of developing interstitial fibrosis or tubular atrophy which comprises:
    obtaining a post-transplant urine sample from the kidney transplant recipient;
    measuring the level of clusterin in the urine sample;
    comparing the level of clusterin in the patient sample to the level of clusterin in a control sample from the urine of a non-fibrotic kidney transplant recipient;
    diagnosing a kidney transplant recipient with a clusterin level that is significantly higher than the clusterin level in the control as being at an increased risk of developing interstitial fibrosis or tubular atrophy and
    treating the recipient for interstitial fibrosis or tubular atrophy.

2. The method of claim 1 wherein the treatment comprises administering an anti-fibrotic agent to the recipient identified as being at increased risk of developing interstitial fibrosis or tubular atrophy.

3. The method of claim 2 wherein the anti-fibrotic agent is a member selected from the group consisting of Pirfenidone, Relaxin, Bone morphogenetic protein 7 (BMP-7), Hepatocyte growth factor (HGF), and Epoetin delta.

4. The method of claim 1 comprising administering an angiotensin converting enzyme inhibitor (ACEI) to the recipient identified as being at increased risk of developing interstitial fibrosis or tubular atrophy.

5. The method of claim 1 comprising administering an angiotensin II receptor antagonist to the kidney transplant recipient identified as being at increased risk of developing interstitial fibrosis or tubular atrophy.

6. The method of claim 5 wherein said angiotensin II receptor antagonist is losartan.

7. The method of claim 1 comprising administering an immunosuppressive drug to the recipient identified as being at increased risk of developing interstitial fibrosis or tubular atrophy.

8. The method of claim 7 wherein said immunosuppressive drug is a member selected from the group consisting of cyclosporine, tacrolimus, mycophenolate mofetil (MMF) and sirolimus.

9. A method for treating a kidney transplant recipient at an increased risk of developing tubular atrophy which comprises:
    obtaining a post-transplant urine sample from the kidney transplant recipient;
    measuring the level of clusterin in the urine sample;
    comparing the level of clusterin in the transplant recipient urine sample to the level of clusterin in a control sample from the urine of a kidney transplant recipient that is not afflicted with tubular atrophy;
    diagnosing the kidney transplant recipient with a clusterin level that is significantly higher than the clusterin level in the control as being at an increased risk of developing tubular atrophy and treating the patient at an increased risk of developing tubular atrophy.

10. A method for treating a patient at increased risk of developing decreased renal function in a kidney transplant recipient which comprises the steps of:
    obtaining a post-transplant urine sample from the kidney transplant recipient afflicted with tubular atrophy;
    measuring the level of clusterin in the urine sample from the kidney transplant recipient that is afflicted with tubular atrophy;
    comparing the level of clusterin in the sample from the kidney transplant recipient that is afflicted with tubular atrophy to the level of clusterin in a control urine sample from a non-fibrotic kidney transplant recipient;
    diagnosing the kidney transplant recipient that is afflicted with tubular atrophy as being at an increased risk of developing decreased renal function if the clusterin level in said patient's urine sample is more than 50% higher than the clusterin level in the control and treating the patient diagnosed as being at increased risk of developing decreased renal function.

11. The method of claim 10 wherein the treatment comprises administering an anti-fibrotic agent to the recipient identified as being at increased risk of developing decreased renal function.

12. The method of claim 11 wherein the anti-fibrotic agent is a member selected from the group consisting of Pirfenidone, Relaxin, Bone morphogenetic protein 7 (BMP-7), Hepatocyte growth factor (HGF), and Epoetin delta.

13. The method of claim 10 comprising administering an angiotensin II receptor antagonist to the recipient identified as being at an increased risk of developing decreased renal function.

14. The method of claim 13 wherein the angiotensin II receptor antagonist is losartan.

* * * * *